United States Patent [19]

Liebermann et al.

[11] Patent Number: 5,308,363
[45] Date of Patent: May 3, 1994

[54] PROCESS FOR QUATERNARY AMMONIUM BISULFATES

[75] Inventors: George Liebermann, Mississauga; H. Bruce Goodbrand, Hamilton, both of Canada; John L. Haack, Pittsford, N.Y.; John Abate, Mississauga, Canada

[73] Assignee: Xerox Corporation, Stamford, Conn.

[21] Appl. No.: 836,435

[22] Filed: Feb. 18, 1992

[51] Int. Cl.$^5$ ............................................. C07C 211/63
[52] U.S. Cl. ................................. 23/295 R; 430/110; 564/291; 564/295
[58] Field of Search ................. 23/295; 430/110; 564/291, 296

[56] References Cited

U.S. PATENT DOCUMENTS

| | | | |
|---|---|---|---|
| Re. 32,883 | 3/1989 | Lu | 430/110 |
| 3,893,935 | 7/1975 | Jadwin et al. | 252/62.1 |
| 4,058,585 | 11/1977 | MacKay et al. | 423/24 |
| 4,221,856 | 9/1980 | Lu | 430/110 |
| 4,291,111 | 9/1981 | Lu | 430/107 |
| 4,291,112 | 9/1981 | Lu | 430/110 |
| 4,298,672 | 11/1981 | Lu | 430/108 |
| 4,312,933 | 1/1982 | Lu | 430/122 |
| 4,560,635 | 12/1985 | Hoffend et al. | 430/106.6 |
| 4,675,118 | 6/1987 | Stanley et al. | 252/8.8 |
| 4,752,550 | 6/1988 | Barbetta et al. | 430/106.6 |
| 4,812,381 | 3/1989 | Bugner et al. | 430/110 |
| 4,904,762 | 2/1990 | Chang et al. | 430/110 |
| 4,937,157 | 6/1990 | Haack et al. | 430/110 |
| 5,045,423 | 9/1991 | Weber et al. | 430/110 |
| 5,082,758 | 1/1992 | Hoffend et al. | 430/126 |
| 5,114,821 | 5/1992 | Haack | 430/110 |

*Primary Examiner*—Gary P. Straub
*Attorney, Agent, or Firm*—John L. Haack; Eugene O. Palazzo

[57] ABSTRACT

A process for the preparation of a quaternary ammonium bisulfate which comprises the reaction of a quaternary ammonium alkylsulfate with sulfuric acid in a solvent mixture comprised of water and isopropyl alcohol, followed by the recovery of the solid quaternary ammonium bisulfate by crystallization from the reaction mixture.

11 Claims, No Drawings

PROCESS FOR QUATERNARY AMMONIUM BISULFATES

BACKGROUND OF THE INVENTION

This invention is generally directed to processes for the preparation of quaternary ammonium compounds, and more specifically to economically feasible, large scale processes for the preparation of quaternary ammonium bisulfates. More specifically, the present invention is directed to the preparation of quaternary ammonium bisulfates, especially hydrogen sulfates, such as distearyl dialkyl ammonium bisulfates, by the reaction of the appropriate ammonium salt with sulfuric acid in a specific solvent mixture. The resulting products can be selected as additives, especially charge control additives for toner compositions, and in embodiments may be useful as antifungal components and surface active agents such as phase transfer catalysts. In developer and toner compositions, the aforementioned charge control additives impart or assist in imparting a positive charge to the toner resin particles and enable toners in some instances with rapid admix characteristics. These toner compositions usually contain pigment particles comprised of, for example, carbon black, magnetites, or mixtures thereof, cyan, magenta, yellow, blue, green, red, or brown pigments, or mixtures thereof, thereby providing for the development of black and/or colored images in electrophotographic, especially xerographic, imaging and printing processes, including color processes.

Developer compositions with charge enhancing additives, and processes for the preparation thereof in some instances, which additives impart a positive charge to the toner resin, are known. Thus, for example, the use of quaternary ammonium salts as charge control agents for electrostatic toner compositions is described in several U.S. Pat. Nos. such as: 3,893,935; 4,221,856; 4,312,933, a division of U.S. Pat. No. 4,291,111; 4,291,112; 4,298,672; 4,560,635; 4,675,118 and 4,812,381.

Toner and developer compositions with the quaternary ammonium salt compounds of the present invention are specifically illustrated in U.S. Pat. No. 4,937,157, the disclosure of which is totally incorporated herein by reference. Further, there are illustrated in U.S. Pat. No. 4,904,762, the disclosure of which is being totally incorporated herein by reference, toner and developer compositions comprised of a mixture of charge enhancing additives wherein one of the additives is an alkylammonium bisulfate as described herein.

Quaternary ammonium bisulfates (hydrogen sulfates) and methods of preparing thereof are described in the literature. A number of bisulfates with the generic formula $(R^1)_3R^2N^+HSO_4^-$, and more specifically tetraalkylammonium bisulfates ($C_3$-$C_6$) and aryltrialkylammonium bisulfates, and methods for the preparation thereof are described by A. E. Brandstrom et al. in U.S. Pat. No. 3,816,533. In a first synthetic scheme, a quaternary ammonium iodide was obtained from an alkyl iodide and the corresponding alkylamine in acetonitrile, and then reacted with dimethyl sulfate to produce a tetraalkyl or aryltrialkylammonium methylsulfate. After removal of the solvent by distillation, water and a catalytic amount of sulfuric acid was added and the mixture was allowed to boil for 24 hours while distilling off methanol. Subsequent to evaporation to dryness, the crude bisulfate was purified by recrystallization. A second route involves the reaction of a tetraalkylammonium hydroxide with a molar equivalent of sulfuric acid, the evaporation of the resulting solution to dryness and the recrystallization of the crude bisulfate from methyl ethyl ketone. In another method described in U.S. Pat. No. 3,816,533, a tetraalkylammonium bromide is reacted with pentachlorophenol in a two phase organic-aqueous solvent system in the presence of sodium hydroxide. The resulting tetraalkylammonium phenolate is then reacted with aqueous sulfuric acid, the aqueous solution evaporated and the bisulfate found in the residue reprecipitated from a solvent such as methyl isobutyl ketone. Yet another method described in the aforementioned U.S. patent involves the preparation of certain quaternary ammonium bisulfates by reacting a quaternary ammonium halide with sulfuric acid and hydrogen peroxide. The reaction mixture can be filtered, the filtrate evaporated in vacuum and the residue redissolved in an organic solvent to recover the bisulfate by recrystallization.

A variant of the aforementioned first method, that is the dimethyl sulfate method, Is detailed in "Preparative Ion Pair Extraction", Apotekarsocieteten/Hassle, Lakemedel, Sweden, 1977, pages 139 to 148 by A. Brandstrom and reproduced by C. M. Starks and C. Liotta in "Phase Transfer Catalysis, Principles and Techniques", Academic Press, New York, 1978, pages 76 to 77. This procedure involves the Use of several organic solvents in a multi step process, in particular chlorobenzene, dioxane and petrol ether.

An ion pair extraction method is also described in the aforementioned textbooks. For example, a tetraalkyl ammonium iodide, trioctylamine and sulfuric acid are reacted in a two phase toluene-water solvent system. The aqueous phase containing the bisulfate is extracted with an organic solvent such as methylene chloride to remove excess tetraalkyl ammonium halide and the excess of sulfuric acid as an ion pair with trioctylamine. Water was removed at reduced pressure and the residue was recrystallized from methyl isobutyl ketone to obtain the pure quaternary ammonium bisulfate.

Dehmlow et al. in Syntheses, 1985, pages 508 to 509, indicates that most of these methods work well for tetrabutyl ammonium derivatives, but they cannot be extended to more hydrophobic (lipophilic) ammonium bisulfates. Alternative methods for obtaining more hydrophobic tetraalkyl ammonium bisulfates were pursued by Dehmlov et al. One of these methods involves the synthesis of tetraalkyl ammonium thiocyanates and their reaction with relatively concentrated sulfuric acid. Byproducts of the reaction include $H_2S$, $CO_2$, $CS_2$ and HSCN, and a rather involved work-up procedure is required to isolate the bisulfate. Another method, described by De Giorgi et al., *Synthetic Communications*, 17(5), 1987, pages 52 to 533, requires the reaction of sulfuric acid with quaternary ammonium azides. The quaternary ammonium azides, in turn, have to be prepared from quaternary ammonium methane sulfonates by reaction with sodium azides.

The prior art methods are rather complicated, not easily conducive to scale-up, nor do these methods usually provide for an economically feasible commercial process, problems avoided or minimized with the processes of the present invention.

Another procedure for Producing quaternary ammonium hydrogen sulfate, specifically tetrabutylammonium hydrogen sulfate, is described in U.K. Patent Application 2,073,748. The method proposed involves the reaction of quaternary ammonium halide with sulfuric acid in the presence of an alcohol. After completing the reaction by heating to reflux, the byproduct, butyl bromide, was removed by distillation together with some of the alcohol used in the reaction. The proposed recovery of the bisulfate from the residue involves the extraction with methylene chloride, evaporation to dryness of the organic phase and recrystallization from methyl isobutyl ketone.

Disclosed in copending patent application U.S. Ser. No. 396,497 now abandoned, the disclosure of which is totally incorporated herein by reference, the disclosure of which is totally incorporated herein by reference, is a process for the preparation of distearyl dimethyl ammonium bisulfate by a process for the preparation of quaternary ammonium compounds of the formula $R'_2R''_2N^+X^-$ wherein R' and R'' are independently selected from the group consisting of alkyl, aryl, and alkylaryl; and X- is an anion, which comprises the reaction by heating a water insoluble quaternary ammonium salt with an acid.

SUMMARY OF THE INVENTION

It is an object of the present invention to provide processes for the preparation of quaternary ammonium bisulfates which are simple, use readily available raw materials and can be selected for pilot plant scale-up and commercial scale manufacturing.

Another object of the present invention is to provide processes for the preparation of quaternary ammonium bisulfates in which these compounds are obtained and isolated as high, up to for example 99.5 percent purity, in a thermally stable solid form, with a certain acceptable melting point.

It is yet another object of the present invention to provide processes for the manufacture of hydrophobic quaternary ammonium bisulfates in which processing issues such as formation of gels, or other water containing complexes typical for this class of compounds, evaporation to complete dryness, and other large scale process aspects are avoided, or minimized.

These and other objects of the present invention can be achieved by providing a simple and robust process for the preparation of quaternary ammonium bisulfates. More specifically, the present invention is directed to the preparation of certain quaternary ammonium bisulfate salts from the corresponding quaternary ammonium alkylsulfates with 1 to about 20 carbon atoms, such as methylsulfates or ethylsulfates, many of which are commercially available, or can be easily synthesized by known methods. Commercially available quaternary ammonium alkylsulfates include, for example, distearyldimethylammonium methylsulfate produced by Sherex Chemical Company as VARISOFT 190 ® and by Hexcel Company as SUMQUAT 60458 ®.

One embodiment of the present invention comprises the rapid and simple reaction of the quaternary ammonium alkylsulfate with sulfuric acid in a specific solvent system containing water and isopropyl alcohol, or isopropanol, especially an 80 to 20 weight percent isopropanol to water mixture. The solvent mixture of the present invention can be selected to avoid the formation of gels or semigelatinous products which can occur when the reaction is accomplished in an aqueous system which renders large scale and isolation of the final product difficult. In one embodiment of the present invention, the composition of the reaction solvent system comprised of water and isopropanol is selected to enable the recovery of the formed quaternary ammonium bisulfate by crystallization upon cooling the reaction mixture to room temperature, after performing the reaction at between 400° C. to 1000° C. for 1 to about 4 hours.

In another embodiment of the present invention, in the reaction of the quaternary ammonium alkyl sulfate with sulfuric acid, the amount of sulfuric acid is selected in the range from 0.5 to 10 molar equivalent to 1 equivalent of the quaternary ammonium alkylsulfate to obtain, for example, an optimum crystallization yield and high product purity.

In a specific embodiment of the present invention, the reaction solvent system is prepared by mixing isopropyl alcohol with water in a ratio of from about 1:1 to about 20:1, and preferably from about 3:1 to about 10:1. Concentrated sulfuric acid is then added underagitation and cooling. The amount of sulfuric acid is selected so as to achieve a ratio of about 0.5 to about 10 molar equivalents of acid to 1 molar equivalent of quaternary ammonium alkylsulfate, and preferably about 1 molar equivalent or less of the said acid to 1 molar equivalent of said ammonium alkylsulfate. The quaternary ammonium alkylsulfate is then added and the reaction initiated by heating the reaction mixture under agitation to from between about (about as used herein includes between about) 40° to about 1000° C. for about one to four hours, or other effective timed period. The time, temperature profile of the reaction may be selected, for example, as a function of the boiling temperature of the solvent system used, as a reaction under reflux offers a convenient temperature control of the process. After the reaction is completed, a gradual cooling over a period of, for example, about 10 minutes or other effective times in embodiments is applied to effect a controlled crystallization of the quaternary ammonium bisulfate.

Following the crystallization of the quaternary ammonium bisulfate from the reaction mixture upon cooling, the solid product is separated by filtration and it can be easily purified by a number of methods to obtain a high purity quaternary ammonium bisulfate with a well defined melting point as the major thermal transition peak identified by Differential Scanning Calorimetry (DSC), IR spectra, and minimum water content. The material recovered by filtration from the reaction mixture can thus be purified by several, up to about 10 for example, reslurry washings with a solvent mixture containing water and isopropanol to remove the acidic species and other impurities. A sequential washing procedure involving the reuse of the washes in optional subsequent washing steps can be selected to assure the high purity of the final product while minimizing waste and maximizing the recovered yield. The purified material is then dried at a temperature of from about 65° to about 75° C. under full vacuum until a constant weight of product is obtained. To increase the drying process time and reduce the water content of the final product, an acetone wash can be performed prior to the drying step. In another purification route, the product recovered by crystallization can be isolated by recrystallization from an organic solvent, such as acetone, isopropyl alcohol and the like.

Embodiments of the present invention include a process for the preparation of a quaternary ammonium bisulfate which comprises the reaction of a quaternary ammonium alkylsulfate with sulfuric acid in a solvent mixture comprised of water and isopropyl alcohol, followed by the recovery of the solid quaternary ammonium bisulfate by crystallization from the reaction mixture, and wherein the quaternary ammonium alkylsulfate is, for example, a quaternary ammonium methylsulfate, and the product is a quaternary ammonium bisulfate of the formula $R'_2R''_2N^+HSO_4^-$ wherein $R'$ and $R''$ are independently selected from the group consisting of alkyl with, for example, from 1 to about 20 carbon atoms, such as methyl, ethyl, propyl, butyl, propyl, pentyl, hexyl, decyl, and the like, aryl with, for example, from 6 to about 24 carbon atoms such as phenyl, naphthyl, and the like, and alkylaryl; and in embodiments wherein the ratio of isopropyl alcohol to water is from about 75 to 25 weight percent to about 90 to 10 weight percent.

The following Examples are being supplied to further define the present invention, it being noted that these examples are intended to illustrate and not to limit the scope invention. Comparative Examples I and II are also provided. Comparative Examples I and II and Example III describe the synthesis of distearyl dimethyl ammonium bisulfate by reacting distearyl dimethyl ammonium methylsulfate with sulfuric acid using three solvent systems: water, a mixture of water and methanol, and a mixture of water and isopropanol, the solvent system of the present invention. The major advantages of the water and isopropanol solvent system is related to the significantly improved product isolation/filtration characteristics evidentiated by a ten-fold improvement in the filtration time. This can be significant with large scale manufacturing methods where filtration times are much longer then in the laboratory due to the filter area limitations. Other advantages include a higher purity product as shown by melting point, water content and bisulfate content, all of which can be important quality control factors in large scale commercial processes. Examples IV and V illustrate large scale processes according to the present invention which also include the advantage of solvent recycling.

COMPARATIVE EXAMPLE I

In a 1 liter 3-necked round bottomed flask equipped with a mechanical stirrer and reflux condenser were suspended 60 grams (90.8 millimoles) of distearyl dimethyl ammonium methylsulfate in 225 grams of deionized water. Nine and 57 hundreds (9.57) grams of 95 percent sulfuric acid (90.8 millimoles) were then added and the reaction mixture was heated to 700° C. for 4 hours. The resulting clear, relatively viscous creamy yellow solution was then cooled slowly. After about 45 minutes at about 400° C., the viscosity of the mixture increased significantly as gel formation was observed. At about 30° C. the gellatinous mass could not be stirred due to the formation of a semi-solid, then a solid gel. As the material did not crystallize, it had to be removed, in small portions, as a gel from the flask, an undertaking not feasible in a large scale reactor, such as a 1,000 to 5,000 gallon stainless steel reactor. A gelled reaction mixture of the quaternary ammonium bisulfate is undesired from a product recovery point of view as it cannot be readily discharged from the reactor and the recovery of the solid bisulfate from the solidified gel would be technically and economically unpractical.

COMPARATIVE EXAMPLE II

In a 1 liter 3-necked round bottomed flask equipped with a mechanical stirrer and reflux condenser were suspended 60 grams (90.8 millimoles) of distearyl dimethyl ammonium methylsulfate in a mixture of 168.75 grams of methanol and 56.25 grams of deionized water. 9.57 grams of 95 percent sulfuric acid (90.8 millimoles) were then added and the reaction mixture was heated at gentle reflux, at about 71° to 72° C., for 4 hours. The resulting cloudy, emulsion-like mixture was then cooled slowly. After about one hour of slow cooling at about 350° C., droplets formation was observed and at about 300° C. solid particles formation was noticed. The crystallization was continued overnight, about 18 hours, under agitation at about 20° to 25° C. The waxy slurry was filtered under vacuum on an 11 centimeter Whatman #4,filter paper on a Buchner funnel. The filtration time recorded was 20 minutes. The filter cake was reslurried In 225 grams of a 75/25 mixture of methanol and water to remove residual acidity. The mixture of methanol and water was used in order to attempt to avoid the formation of gel experienced when water only is used to wash the highly acidic wet cake. A waxy, semigelatinous slurry was obtained, which required 20 minutes to filter. One additional reslurry washing was accomplished as described above requiring a filtration time of 35 minutes. A final reslurry wash with 225 grams of acetone was accomplished after which the product was recovered by filtration and dried overnight in vacuum at about 50° C. 41.7 grams (71.0 percent yield) of distearyl dimethyl ammonium bisulfate was recovered. Analyticals: melting point (DSC) 93.1° C., $H_2O$ content 0.11 percent, bisulfate content (by titration) 14.22 percent (theoretical 14.99 percent). and a different IR fingerprint from the material of COMPARATIVE Example I.

EXAMPLE III

In a 1 liter 3-necked round bottomed flask equipped with a mechanical stirrer and reflux condenser were suspended 60 grams (90.8 millimoles) of distearyl dimethyl ammonium methylsulfate in a mixture of 168.75 grams of isopropanol and 56.25 grams of deionized water. 9.57 grams of 95 percent sulfuric acid (90.8 millimoles) were then added and the reaction mixture was heated at gentle reflux, at about 820° C., for 4 hours. The resulting clear, orange-yellow solution was then cooled slowly. After about one hour, at about 30° C., crystals started to appear, followed by a massive crystallization with a noticeable exotherm of over 4° C. and the formation of white viscous slurry The crystallization was continued overnight, about 18 hours, under agitation at about 20° to 25° C. The slurry was filtered under vacuum on an 11 centimeter Whatman #4 filter paper with a Buchner funnel. The filtration time recorded was 2 minutes. The excellent filtration rate reflects the excellent crystallization characteristics of the product. A white filter cake was obtained, while a yellowish filtrate was removed. The filter cake was reslurried in 225 grams of a 75/25 mixture of isopropanol and water to remove residual acidity. The mixture of isopropanol and water was used to avoid the formation of gel experienced when water only is used to wash the highly acidic wet cake. A white slurry was obtained, which again required only 2 minutes to filter. Two more reslurry washings were accomplished as described above with filtration times of about 2 minutes each. A final reslurry wash with 200 grams of acetone was accomplished after which the product was recovered by filtration and dried overnight in vacuum at about 50° C. 42.7 grams (72.7 percent yield) of distearyl dimethyl ammonium bisulfate (IR fingerprint) were recovered. Analyticals- melting point (DSC) 94.50° C., H₂O content 0.04 percent, bisulfate content (by titration) 15.24 percent.

EXAMPLE IV

Seventy-five (75) kilograms of isopropyl alcohol and 25 kilograms of deionized water were charged in a 50 gallon glass lined reactor. The reactor agitator (three armed retrieve curve impeller) was started at 100 RPM and full cooling (water at 8° to 10° C.) was applied to the reactor jacket. Eighteen (18) kilograms of 93 percent sulfuric acid (technical grade) were added slowly to the reactor, after which 30 kilograms of technical grade distearyl dimethyl ammonium methylsulfate (obtained from Zeeland Chemical Co., d Cambrex Company formerly Hexcel Company of Zeeland, Mich.) were charged in the reactor. The reactor loading port was closed and cooling water was applied to the reactor reflux condenser and the agitator speed adjusted to 150 RPM. The reactor was heated to approximately 840° C. using hot water supplied to the reactor jacket. The reaction was effected for 4 hours under a slight reflux after which cooling was applied to initiate the crystallization. The mixture was agitated for two hours under full cooling at 16° to 18° C. before transferring to a 70 gallon agitated Nutsche vacuum filter. The filtrate was drained and collected in a storage vessel for solvent recovery or disposal. The wet cake was reslurried with 100 kilograms of the second wash filtrate from the previous batch (containing an approximate 75:25 ratio of isopropanol and water) for 30 minutes, after which the filtrate (about 100 kilograms) was drained by vacuum filtration and collected in order to be used as the solvent system for the next synthesis batch. After additional reslurry washes were performed using wash filtrates from a previous batch, the wet cake was discharged from the filter and recrystallized from 100 kilograms of isopropanol In a 50 gallon glass lined reactor. This was performed by dissolving the materials under agitation at 600° C., cooling and recovering the wet dimethyl distearyl ammonium bisulfate cake by filtration. After vacuum drying, 22.27 kilograms (75.8 percent yield) of recrystallized distearyl dimethyl ammonium bisulfate were recovered. Analyticals: melting point (DSC) 91.4° C., H₂O content 0.65 percent, bisulfate content (by titration) 14.65 percent.

EXAMPLE V

One hundred (100) kilograms of a solution containing approximately an 80:20 ratio of isopropyl alcohol and water, which was used as a first wash in a previous synthesis batch, were charged in a 50 gallon glass lined reactor. The reactor agitator (three arm retrieve curve impeller) was started at 100 RPM and full cooling (water at 15° to 200° C.) was applied to the reactor jacket. Four and five tenths (4.5) kilograms of 93 percent sulfuric acid (technical grade) were slowly added to the reactor, after which 30 kilograms of technical grade distearyl dimethyl ammonium methylsulfate were charged in the reactor, the reactor loading port was closed and cooling water was applied to the reactor reflux condenser and the agitator speed adjusted to 150 RPM. The reactor was heated up to approximately 80° C. using hot water supplied to the reactor jacket. The reaction was carried out for 4 hours under a slight reflux. Cooling was started at a rate of approximately 1° C. per minute in order to assure a good crystallization. At about 300° C. full cooling for two hours (approximately 20° C. in reactor) was accomplished, after which the slurry was transferred in a 70 gallon agitated Nutsche vacuum filter. The filtrate was removed and collected in a storage vessel for solvent recovery or disposal.

The wet cake was reslurried in the mechanically agitated Nutsche filter with 100 kilograms of the second wash filtrate from the previous batch (containing approximately an 80:20 ratio of isopropyl alcohol) for 30 minutes, after which the filtrate (~100 kilograms) was drained by vacuum filtration and collected in order to be used as the solvent system for the next distearyl dimethyl ammonium bisulfate synthesis.

A second reslurry wash was performed using a fresh mixture of 80 kilograms of isopropyl alcohol and 20 kilograms of deionized water in a similar fashion. The pH of this wash was checked to insure that the residual acidity was removed and the pH was equal to or less than 1.65. The second wash filtrate was stored for use as first wash in the next batch. The nonfiltrate was reslurried again with 80 kilograms of acetone. The acetone was drained and stored for future use.

The acetone containing wet cake was discharged in a double cone rotary vacuum dryer and dried for several hours under vacuum with the dryer temperature gradually increased to 70° to 75° C. 24.32 kilograms of distearyl dimethyl ammonium bisulfate (82.8 percent yield) were obtained. Analyticals: m.p. 93.9° C., H₂O content 0.16 percent, bisulfate content (by titration) 15.63 percent.

Other embodiments and modifications of the present invention may occur to those skilled in the art subsequent to a review of the information presented herein; these embodiments and modifications, as well as equivalents thereof, are also included within the scope of this invention.

What is claimed is:

1. A process for the preparation of a quaternary ammonium bisulfate which consists essentially of the reaction of a quaternary ammonium alkylsulfate with sulfuric acid in solvent mixture comprised of water and isopropyl alcohol, wherein the isopropyl alcohol is present in an amount of about 80 weight percent, and the water is present in an amount of 20 weight percent based on the total weight of the solvent mixture, followed by the recovery of the solid quaternary ammonium bisulfate by crystallization from the reaction mixture.

2. A process in accordance with claim 1 wherein the quaternary ammonium alkylsulfate is a quaternary ammonium methylsulfate.

3. A process in accordance with claim 1 wherein the quaternary ammonium bisulfate is of the formula $R'_2R''_2N^+HSO_4^-$ wherein $R'$ and $R''$ are independently selected from the group consisting of alkyl, aryl, and alkylaryl.

4. A process in accordance with claim 1 wherein the quaternary ammonium alkylsulfate is selected from the group consisting of distearyl dialkyl ammonium methylsulfates wherein the alkyl group contains from 1 to about 20 carbon atoms.

5. A process in accordance with claim 1 wherein the reaction is accomplished at a temperature of from about 40° to about 100° C.

6. A process in accordance with claim 1 wherein from 0.5 to 1.0 molar equivalents of sulfuric acid to 1 molar equivalent of quaternary ammonium alkylsulfate reactant is selected.

7. A process in accordance with claim 1 wherein the sulfuric acid is selected in an amount of from about 0.5 equivalents to about 10 molar equivalents of quaternary ammonium alkylsulfate.

8. A process in accordance with claim 1 wherein the product recovered by filtration is purified by reslurry washings with a solvent containing water and isopropanol.

9. A process in accordance with claim 8 wherein the product is purified with acetone prior to drying.

10. A process in accordance with claim 1 wherein the quaternary ammonium compound product resulting is distearyl dimethyl ammonium bisulfate.

11. A process in accordance with claim 1 wherein alkyl contains from 1 to about 20 carbon atoms.

* * * * *